(12) United States Patent
Escalier et al.

(10) Patent No.: US 10,548,473 B2
(45) Date of Patent: Feb. 4, 2020

(54) OPTOMETRY MEASURING SCALE

(71) Applicant: Essilor International, Charenton-le-Pont (FR)

(72) Inventors: Guilhem Escalier, Charenton-le-Pont (FR); Gildas Marin, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/570,230

(22) PCT Filed: Jun. 23, 2015

(86) PCT No.: PCT/IB2015/001562
§ 371 (c)(1),
(2) Date: Oct. 27, 2017

(87) PCT Pub. No.: WO2016/207684
PCT Pub. Date: Dec. 29, 2016

(65) Prior Publication Data
US 2018/0116500 A1    May 3, 2018

(51) Int. Cl.
*A61B 3/02*   (2006.01)
*A61B 3/036*  (2006.01)
(Continued)

(52) U.S. Cl.
CPC .............. *A61B 3/036* (2013.01); *A61B 3/02* (2013.01); *A61B 3/022* (2013.01); *A61B 3/032* (2013.01);
(Continued)

(58) Field of Classification Search
CPC ..... A61B 3/032; A61B 3/0025; A61B 3/0041; A61B 3/02; A61B 3/022; A61B 3/036;
(Continued)

(56) References Cited

U.S. PATENT DOCUMENTS

2014/0211164 A1* 7/2014 Nakamura ............. A61B 3/032
351/221

FOREIGN PATENT DOCUMENTS

| EP | 1 138 251 A1 | 10/2001 |
| EP | 1 250 883 B1 | 10/2002 |
| WO | 2014/195951 A1 | 12/2014 |

OTHER PUBLICATIONS

Juan Tabernero et al: "An aspheric intraocular telescope for age-related macular degeneration patients", Biomedical Optics Express, vol. 6, No. 3, Feb. 25, 2015 (Feb. 25, 2015), p. 1010, XP055253287, United States.
(Continued)

*Primary Examiner* — Brandi N Thomas
(74) *Attorney, Agent, or Firm* — Young & Thompson

(57) ABSTRACT

Disclosed is an optometry measuring scale and method for determining a visual refraction value of an individual. According to the invention, the optometry measuring scale comprises a plurality of processed optotypes associated with a plurality of visual refraction corrections, wherein each processed optotype results from applying to a source optotype a determined image processing associated with a defined visual refraction correction, and an identification system for determining each defined visual refraction correction associated with each processed optotype.

19 Claims, 3 Drawing Sheets

(51) Int. Cl.
  *A61B 3/032* (2006.01)
  *G02B 27/22* (2018.01)
  *H04N 13/305* (2018.01)

(52) U.S. Cl.
  CPC ....... *G02B 27/2214* (2013.01); *H04N 13/305* (2018.05)

(58) Field of Classification Search
  CPC ..... A61B 3/0008; A61B 3/103; A61B 3/0033; A61B 3/08; A61B 3/1015; A61B 3/113; A61B 3/12; A61B 2560/0475; A61B 2562/0219; A61B 2562/0223
  USPC ........ 351/233, 200, 205–206, 209–211, 221, 351/222, 243–246
  See application file for complete search history.

(56) References Cited

OTHER PUBLICATIONS

Kodikullam V. Avudainayagam et al: "Performance of the holographic multivergence target in the subjective measurement of spherical refractive error and amplitude of accommodation of the human eye", Journal of the Optical Society of America A, vol. 24, No. 10, Oct. 1, 2007 (Oct. 1, 2007), pp. 3037-3044, XP055253020, United States.

International Search Report dated Mar. 7, 2016, in corresponding PCT application.

\* cited by examiner

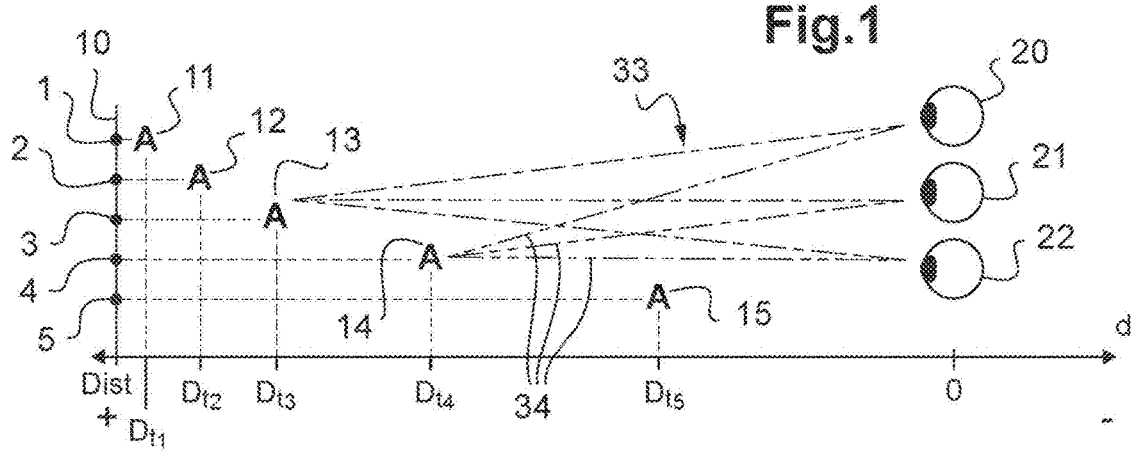

Fig.6

| 6E | 6F | 6G | 6H (6K: 0D, 1D, 2D, 3D) | | | |
|---|---|---|---|---|---|---|
| | | | 0D | 1D | 2D | 3D |
| E | ✱⁻¹ | 3D | | | | |
| | | 2D | | | | |
| | | 1D | | | | |
| | | 0D | | | | |
| | | -1D | | | | |
| | | -2D | | | | |
| | | -3D | | | | |

Fig.7

| 7E | 7F | 7G | 7H |
|---|---|---|---|
| E Ǝ m ɯ | ✱⁻¹ | 3D (-) | E Ǝ m ɯ |
| | | 2.5D (0D) | E Ǝ m ɯ |
| | | 2D (0.5D) | E Ǝ m ɯ |
| | | 1.5D (1D) | E Ǝ m ɯ |
| | | 1D (1.5D) | E Ǝ m ɯ |
| | | 0.5D (2D) | E Ǝ m ɯ |
| | | 0D/(>=2.5D) | E Ǝ m ɯ |

OPTOMETRY MEASURING SCALE

TECHNICAL FIELD OF THE INVENTION

The invention relates to a device and a method for screening the need of visual correction of persons.

More precisely, the invention relates to a device and a method for evaluating the eye refraction and/or for testing astigmatism of a person.

BACKGROUND INFORMATION AND PRIOR ART

Numerous documents describe devices and methods for testing the eyes of a person.

Some devices and methods for testing the eyes are of subjective type, because they require the active assistance of the person. Other devices and methods for testing the eyes are of objective type, because they are independent of the person's perceptions or reactions.

The objective type devices for testing the eyes refraction usually require large, heavy and expensive equipment, such as an autorefractor. Generally, an objective type device needs power supply, is not very reliable or requires the intervention of a qualified person.

Subjective testing can provide precise optometric measurements. However, a normal refraction measurement process is complex and time-consuming (more than 15 minutes per tested person) and requires the intervention of an optometrist and/or a medical specialist.

Subjective devices such as screening charts also exist that are less sophisticated equipment and can be used on a larger basis. As an example, Snellen's, EDTRS or Bailey Lovie acuity charts are well known subjective type devices for testing the eyes of a person. These charts display lines of target alphanumerical characters printed in sharp block letters and placed in lines of decreasing size. A person subject to a visual test is placed at a distance from the chart and reads the target alphanumerical characters from the larger size down to the smallest readable line. The distance between the chart and the person is generally set to more than 3-4 meters for far vision test and to less than 60 cm for near vision test. A scale, displayed at the end of each line, indicates the corresponding visual acuity. The smallest line that can be read by the person accurately indicates the visual acuity of this person, giving thus an evaluation of the refraction correction needed by this person.

This visual test can be performed in monocular or binocular vision conditions, for near vision or far vision test, with or without corrective lenses. These charts require only a printed board and can be used for evaluating the visual acuity of any person able to read the alphanumerical characters displayed.

Other charts dedicated to young children or illiterate persons are based on other target optotypes such as images or symbols that do not require deciphering alphanumerical characters. In all cases, the target optotypes are displayed with a high clearness and contrast (in general black optotypes on a clear background).

However, without the use of any corrective lenses, the estimation of the correction needed is very poor and does not give the type of correction needed (spherical or astigmatism). The use of corrective trial lenses can provide precise optometric measurements. However, a normal refraction measurement process is complex and time-consuming (more than 15 minutes per tested person), requires the use of a full and expensive set of trial lenses and requires the intervention of a skilled person such as an optometrist and/or a medical specialist.

A simple astigmatic test chart, called Parent Dial, allows screening for a particular orientation of an axis of astigmatism. This astigmatic test chart displays a set of line segments disposed radially around a center point, with a constant angular pitch and displays the corresponding angles from 0 to 180 degrees every 10 or 20 degrees, like a protractor. A person subject to a visual test is placed at a distance from the Parent Dial. The target lines are displayed with a high contrast and clearness. However, when the eye of the person presents some degree of astigmatism, some lines are seen sharp and other lines are seen blurred by this person. The person subject to the test indicates the sharpest line seen which corresponds to the orientation of an axis of astigmatism for the tested eye of this person. However, an astigmatic test chart is not very reliable and does not enable, alone, determining the cylindrical degree of correction needed.

Based on an astigmatic test chart, a method for evaluating the cylindrical degree of correction has been developed. The axial angle of astigmatism being determined, a cylindrical lens is inserted on the optical axis between the tested eye and the test chart, the cylindrical axis of this lens being set orthogonal with the axial direction seen clearly. The value of the cylindrical degree C. of the cylindrical lens is adjusted by changing the cylindrical lens power, until the astigmatic test chart is sharply seen uniformly. However, this astigmatic test chart and method requires a set of cylindrical lenses of different optical powers and requires the intervention of a skilled person such as an optometrist and/or a medical specialist.

The patent document EP 1250883_B1 discloses an optometry apparatus comprising a light source, a target object, spherical and/or cylindrical optical lenses and a diffraction grating plate forming different target images that appear to the examined eye(s) dispersed in a plane orthogonal to an optical axis and shown simultaneously at different virtual distances in the direction of the optical axis. However, this system is complex and needs a power supply for the light source.

Another subjective type device is based on a volume phase hologram (Avudainayagam K V, Avudainayagam C S, Nguyen N, Chiam K W, Truong C., *J Opt. Soc. Am. A Opt. Image Sci. Vis.* 2007 October; 24(10):3037-44, "Performance of the holographic multivergence target in the subjective measurement of spherical refractive error and amplitude of accommodation of the human eye"). A complex wavefront arising from illuminating different targets placed at different distances is recorded in a single volume phase hologram. When this hologram is illuminated by a phase conjugated beam, each target forms a three-dimension image having a different vergence in a range from +5 to −2.5 diopters and in steps of 0.5 diopter. From the image target seen clearly by the subject, and the corresponding vergence, the spherical refractive error and the amplitude of accommodation of the human eye can be evaluated. However, this hologram requires a complex illuminating system or setup and can be seen only by one person at a time.

SUMMARY OF THE INVENTION

Therefore one object of the invention is to provide a fast refractive evaluation screening process including an estimation of the correction needed for a person, without an intervention of an optometrist or any other qualified person.

A further object of the invention is to provide a simple device allowing a fast evaluation of the needed correction (sphere S and/or cylinder C and axis A) and without needing intervention of a qualified person. A further object of the invention is to provide a simple device and method enabling vision test of several persons simultaneously in a same place or in different places.

The above objects are achieved according to the invention by providing an optometry measuring scale for determining a visual refraction value of an individual.

According to the invention, the optometry measuring scale comprises a plurality of processed optotypes associated with a plurality of visual refraction corrections, each optotype being associated with a single visual refraction value, wherein each processed optotype results from applying to a source optotype a determined image processing associated with a defined visual refraction correction, and an identification system for determining each defined visual refraction correction associated with each processed optotype.

This optometry measuring scale is a subjective type device for testing the eyes of a person. This optometry measuring scale enables evaluation of eye refraction and/or astigmatism, without requiring any additional optical component such as a set of spherical and/or cylindrical lenses and does not require a complex illuminating system. It can be applied for monocular or binocular vision testing of one or several persons simultaneously. Any person, qualified or non-qualified in optometry, can use it.

According to a particular aspect of the invention, the optometry measuring scale is configured for displaying simultaneously a plurality of processed optotypes, this plurality of processed optotypes being seen simultaneously by a person.

In the present disclosure, an optotype may be a letter, a symbol such as Landolt ring or, more generally, any drawing or sign that may provide sufficient contrast and enough detail to the person when seen sharply, and is preferably designed so that detail resolution is close to the standard eye minimum detail perception.

According to another particular aspect of the invention, the optometry measuring scale further comprises a first and a second processed optotypes associated with a same defined visual refraction correction and, respectively, with a first vision distance and a second vision distance, wherein said first and second processed optotypes result from applying to a source optotype a determined image processing associated with said same defined visual refraction correction and, associated, respectively, with said first vision distance and with said second vision distance.

According to a particular aspect of the invention, said defined visual refraction correction includes a spherical error correction and/or a cylindrical error correction.

According to an embodiment of the invention, said optometry measuring scale comprises an electronic display device and said source optotype comprises a digital image to be displayed on said electronic display device. Preferably, the electronic display device displays images in two dimensions only.

According to an aspect of this embodiment, said determined image processing includes a deconvolution as a function of a predefined visual refraction correction and of a predefined vision distance, or of a predefined display distance.

According to an aspect of this embodiment, said electronic display comprises a light field display comprising at least a multilayer filter or diffractive pattern placed on said electronic display so as to apply a complementary image processing for displaying said processed optotype.

According to another embodiment of the invention, said optometry measuring scale comprises at least one pre-printed chart displaying a plurality of processed optotypes in two dimensions.

According to a particular aspect of the invention, the source optotype is selected among Landolt rings, Snellen's E, alphanumerical characters or images used for measuring visual acuity.

According to a particular aspect of the invention, the processed optotypes are arranged in lines, wherein each line corresponds to a same determined image processing associated with a same defined visual refraction correction applied to one or different source optotype(s).

According to a particular aspect of the invention, the pre-processed optotypes are arranged in lines and columns, wherein each column corresponds to a pre-defined visual refraction parameter chosen among sphere, cylinder, axis and each line corresponds to another pre-defined visual refraction parameter chosen among sphere, cylinder, and axis, wherein the pre-defined visual refraction parameter of the columns is different from the pre-defined visual refraction parameter of the lines.

According to a particular aspect of the invention, the defined visual refraction correction changes gradually from line to line and/or from column to column, by step of 1 diopter, ½ diopter, ¼ diopter or ⅛ diopter.

The invention also concerns the use of an optometry measuring scale for determining a visual refraction correction for a user.

The invention also concerns an optometry measuring method comprising the steps of:
  displaying a plurality of processed optotypes associated with a plurality of visual refraction corrections, wherein each processed optotype results from applying to a source optotype a determined image processing associated with a defined visual refraction correction,
  displaying an identification system for determining each defined visual refraction correction associated with each processed optotype,
  determining the sharpest processed optotype as seen by a user;
  determining a defined visual refraction correction associated with the sharpest processed optotype seen by the user;
  evaluating, from the defined visual refraction correction determined at the previous step, the visual refraction correction needed for the user.

This optometry measuring method is a subjective type method for testing the eyes of a person that enables evaluation of eye refraction and/or for testing astigmatism that requires no additional optical component such as a set of spherical and/or cylindrical lenses.

According to a particular aspect of this optometry measuring method, the processed optotypes are arranged in lines, wherein each line corresponds to a same determined image processing associated with a same defined visual refraction correction applied to one or different source optotype(s).

According to a particular aspect of this optometry measuring method, the defined visual refraction correction changes gradually from line to line, within a range comprised between −10 diopters and +6 diopters, by steps of 1 diopter, ½ diopter, ¼ diopter or ⅛ diopter.

BRIEF DESCRIPTION OF THE DRAWINGS

This description is given for non limiting illustrative purposes only and will be better understood when referring to the annexed drawings wherein:

FIG. 1 represents schematically the principle of operation of an optometry measuring scale according to the invention FIG. 2 represents schematically, starting from an initial image (column 2E) the generation of an exemplary optometry measuring scale (column 2H) as a function of spherical correction between −3 diopters and +3 diopters (column 2G), and this exemplary optometry measuring scale (column 2H) as seen by a person not needing correction and not accommodating FIG. 3 represents the exemplary optometry measuring scale of FIG. 2 as seen by different persons having respectively myopic spherical defect (columns 3I, 3H) or hyperopic spherical defects (column 3J) and not accommodating

FIG. 6 represents schematically, starting from an initial image (column 6E), the generation of another exemplary optometry measuring scale (table 6H) for measuring both spherical correction and astigmatism correction levels;

FIG. 7 represents schematically a test chart for determining accommodation amplitude/addition at near distance, as seen by an emmetrope person having 1.5 diopters accommodation amplitude.

DETAILED DESCRIPTION OF EXAMPLE(S)

Device

Figure 4:
FIG. 4 represents the same exemplary optometry measuring scale as seen by different persons having respectively myopic spherical defect (column 4H) myopic and accommodating (column 4I) and hyperopic spherical defect and accommodating (column 4J)

FIG. 1 represents schematically a side view of a device for testing the eyes of a person 20 or several persons 21, 22.

The device comprises a support 10 that can be a simple printed chart on paper or on cardboard or an electronic display device. The support 10 is placed at a real distance (Dist) from the eye(s) of a person 20 to be tested for visual refraction error.

The support 10 comprises a plurality of processed optotypes 1, 2, 3, 4, 5 and a scale of fixed optical defect values corresponding to visual refraction correction. Preferably, the processed optotypes are arranged in lines on the support 10, each line corresponding to processed optotypes which are pre-compensated for a given fixed optical defect. Each line is pre-compensated according to a different visual refraction correction value. For example, the optical defect corresponds to a spherical error ranging from non compensation (or zero diopter or 0D) to −10 D by constant steps of 0.5 D or 1 D between adjacent lines. The corresponding visual refraction correction is displayed at one end of each line.

The plurality of processed optotypes is generated starting from a well known target or source optotype to which different image processing are applied as a function of each fixed visual refraction correction value.

Within the present disclosure, a processed optotype results from an image processing or image transformation applied to a source optotype having high contrast and high clearness (or sharp edges).

As an example, the image processing corresponds to a deconvolution function based on a visual refraction correction value of defined optical power.

Each processed optotype forms a modified target in the plane of the support 10. A conventional light source, such as day light or a usual lamp, illuminates the support including the plurality of processed optotypes. Each modified target constitutes a secondary source for image formation by the optical system of the observer's eye, which forms a virtual image of each processed optotype at a different distance from the observer than the real distance to the support.

The processed optotype and the eye of the observer cooperate so that the virtual image is compensated for a given fixed visual refraction correction at a given distance from the observer 20, 21, 22. In other words, a compensated image appears clearly and sharply to the eye of an observer not accommodating and having the same visual refraction defect value as the visual refraction correction applied to the processed image corresponding to the virtual image seen clearly.

More precisely, a visual refraction correction value P (corresponding level of correction in the chart) is defined in diopters as follow:

$$P = 1/\text{Dist} - 1/D_{target}$$

where Dist represents the physical distance between the support 10 and the observer 20, 21, 22, and, respectively, $D_{target}$ represents the virtual distance between the observer and the virtual image of a processed optotype. It can be noticed that a lens placed just in front of the eye of the observer, having a power equal to the value P, would also provide and image at a distance $D_{target}$, when observing a standard display placed at a distance Dist. So a lens placed in front of the eye and having optical power P would provide a similar effect.

When testing far vision, the observer is placed at a distance Dist of at least three to four meters from the support, to avoid accommodation. In this case, P is approximately equal to $-1/D_{target}$. This distance is obtained by physically placing the display at distance, for example when using a tablet/smartphone, computer display. Alternatively, this distance may be obtained using a close display associated with a positive power lens that provides a virtual image at distance, for example for HMD eyewear.

For example, for far vision test, a corresponding level of correction of −3 D (P=−3 D) means that $D_{target}$ is +33 cm.

On FIG. 1, a processed optotype 1 corresponds to an initial target without transformation or, in other words, with a transformation of null value. When illuminated by a light beam, and seen by the eye of an observer 20, the processed optotype 1 forms an image 11 in the same plane as the support 10, at a distance $d_{t1}$ equal to Dist from the observer 20.

In contrast, the other lines on the support comprise different processed optotypes 2, 3, 4, 5 according to different non-null values of spherical refraction error. When illuminated by a conventional light beam the eye of an observer 20 forms a virtual image 12 of the processed optotype 2. This virtual image 12 is compensated for a spherical error of −0.5 diopter or, equivalently, at a virtual distance $d_{t2}$ from the observer 20. Respectively, the eye of the observer 20 forms a virtual image 13 of the processed optotype 3, this virtual image 13 being compensated for a spherical error of −1 diopter or, equivalently, at a virtual distance $d_{t3}$ from the observer 20. The eye of the observer 20 forms a virtual image 14 of the processed optotype 4, this virtual image 14 being compensated for a spherical error of −1.5 diopter or, equivalently, at a virtual distance $d_{t4}$ from the observer 20. Finally, the eye of the observer 20 forms a virtual image 15 of the processed optotype 5, this virtual image 15 being compensated for a spherical error of −2 diopters or, equivalently, at a virtual distance $d_{t5}$ from the observer 20.

As a result, an observer 20 having the same visual refraction correction as one of the spherical refraction error values applied for generating one of the processed optotypes and observing this virtual image, the observer 20 being at a distance Dist from the support 10, sees a clear and sharp virtual image of this modified optotype.

The angular field of view (horizontal and/or vertical) of the device is large, and preferably larger than ±45 degrees from the normal to the surface of the support 10. Thus, each virtual image 11-15 can be observed simultaneously from multiple optical axes, for example by several observers 20-22 simultaneously.

For example, the observer 20 has a spherical refraction error of −1 diopter and observes the optometry scale on the support 10 at a distance Dist of at least 3-4 meters. Without corrective lenses, and without accommodating, the observer 20 sees clearly and sharply the image 13 of the processed optotype 3, but sees the images 12, 14 of processed optotypes 2 and 4 slightly blurred, and the images 13, 15 of the processed optotypes 1 and 5 blurred. Another observer 21, having a spherical refraction error of −1.5 diopter and observing the optometry scale on the support 10 at the same distance Dist, not accommodating, sees clearly and sharply the image 14 of processed optotype 4, but sees the images 13, 15 of the processed optotypes 3 and 5 slightly blurred, and the images 11, 12 of the processed optotypes 1 and 2 blurred. Still another observer 22 who does not need any refraction correction, placed at the same distance Dist, sees clearly and sharply the image 11 of processed optotype 1, but sees the images 12, 13 of the processed optotypes 2 and 3 slightly blurred, and the images 14, 15 of the processed optotypes 4 and 5 blurred.

Each observer designates the line that he/she best perceives and thus determines the most appropriate visual correction value corresponding to the best seen line.

It is also possible to conduct the far vision test using the support 10 placed at near vision distance from the subject to be tested, provided that the subject does not accommodate. A second target placed at far distance for directing the eyesight may be used for avoiding accommodation. In this case, the optical power P provided by the processed optotype still follows the rule:

$$P=1/\text{Dist}-1/D_{target}$$

but the quantity 1/Dist must be taken into account. Thus, $1/D_{target}=1/\text{Dist}-P$, and the value of P depends on the distance Dist.

For example, the support 10 is placed at a distance Dist equal to 0.5m from the observer 20. In order to provide a virtual image at a distance of 0.33m in front of the observer (Dtarget=0.33m), corresponding to −3 D myopic vision defect, the visual refraction correction provided by the processed optotype on the support 10 is:

$$P=1/0.5-1/0.33=2-3=-1\ D$$

This result means that the support requires less spherical power correction to achieve the same $D_{target}$ distance as compared to the case where the distance Dist really corresponds to far vision conditions (at least 3-4 meters).

Alternatively, an add-on lens is provided and inserted in the optical beam path between the eye of the observer and the support 10, so that the support 10 is seen at infinity. The support is thus placed in the focal plane of the add-on lens, or, in other words, the power of the add-on lens is the inverse of the distance from the add-on lens to the support 10.

This solution can also be used at other distances, in particular for near vision to determine near vision correction value or addition as compared to far vision correction value.

The two-dimension optometry measuring scale thus enables evaluating far vision and/or near vision correction needed by a person in usual light conditions, without the help of a qualified person.

Different image processing techniques may be employed for generating the processed optotypes. In a first example, the image processing is based on applying a 2 D convolution transform of the processed optotype image and the Point Spread Function (PSF), calculated as the Fourier transform of the complex amplitude function representative of the optical characteristics of the eye as a function of a predefined visual refraction correction and of a predefined vision distance, or of a predefined display distance. An optimization process is then used to find the final processed optotype image to display that will give after convolution the best seen image on the retina. This result is the equivalent of a deconvolution process. The complex amplitude function s is calculated from the optical phase error p using the following equation: s=S*exp(2iPi/lambda*p), where S is the intensity repartition in the pupil, lambda the wavelength. Typically a spherical phase error p corresponding to a spherical power error P can be expressed as a paraboloid function of the position in the pupil: $p(r)=-P*r^2/2$ where r is the distance from the center of the pupil.

In another embodiment, the support 10 represents the screen of a smartphone, a tablet or a computer.

FIG. 2 represents schematically a process for generating of an optometry measuring scale (lines and columns in 2H) for measuring spherical correction between −3 diopters and +3 diopters (scale in column 2G). FIG. 2, column 2E, shows the initial target, or source optotypes. The source optotypes appear clearly in black block letters on a white background, with a high contrast (around 100% contrast) and with sharp edges. In column 2E, the initial target comprises for example a set of four Snellen's E oriented along four different directions. Other optotypes than Snellen's E can be used as source optotypes. For example, alphanumerical characters, Landolt rings or images can be used as source optotypes.

Column 2F represents a computation process used for generating processed optotypes, as a function of different level of corrections displayed in column 2G. Column 2H represents resulting processed optotypes at a far vision distance, as seen by an observer not needing visual correction and not accommodating. The middle line of column 2H corresponds to a line of processed optotypes without modification as compared to the source optotypes in column 2E. In other words, the processed optotypes of this line correspond to processed optotypes processed with a spherical error of 0 diopter (0 D). This middle line of column 2H shows clearly the four Snellen's E for an observer having an emmetrope vision (i.e. not needing visual correction) and not accommodating.

The top line in column 2H corresponds to a line of processed optotypes generated from the source optotype of column 2E and applying (column 2F) a deconvolution algorithm as a function of a spherical error of 3 diopters (or 3 D). In the top line of column 2H, the four Snellen's E can still be recognized, but appear extremely blurred for an observer having an emmetrope vision (i.e. not needing visual correction) and not accommodating.

The second and, respectively third, line in column 2H corresponds to a line of processed optotypes generated from the same source optotype of column 2E and applying (column 2F combined with the corresponding value of column 2G) a deconvolution algorithm as a function of a spherical error of 2 diopters (+2 D), and, respectively of 1 diopter (+1 D).

The other lines below the middle line in column 2H correspond to lines of processed optotypes generated from the source optotype of column 2E and applying (column 2F) a deconvolution algorithm as a function of a spherical error value displayed in column 2G, of, respectively, −1 diopter (−1 D), −2 diopters (−2 D) and −3 diopters (−3 D).

These lines appear increasingly blurred, as a function of increasing spherical error value, for an observer having an emmetrope vision and not accommodating.

The evaluating process can be done binocularly (for a fast determination of an averaged correction of both eyes) or in monocular vision, eye per eye, for a better estimation of the correction needed for each eye.

The main advantage of this method is to enable very quick determination of the mean sphere of ametropia, using very cheap material without the intervention of a qualified person.

In a first embodiment, the support comprises a pre-printed board including several lines of processed optotypes arranged in lines 1, 2, 3, 4, 5. All the lines are displayed simultaneously. The lines can be seen at a large angle of incidence, for example with an angle of incidence of at least ±45 degrees. This pre-printed support enables for a large group of person looking at the same pre-printed support at the same time to be tested simultaneously.

In a second embodiment, the support comprises an electronic display device including its own light source. For example, the electronic display device includes a screen of a smartphone, a tablet or a computer. The electronic display generates virtual images 11, 12, 13, 14, 15 of optotypes at a plurality of virtual distances. The processed optotypes may be generated similarly as described above, by transforming source optotypes using a transform algorithm as a function of a plurality of levels of spherical correction. The processed optotypes may be generated in lines of same values of correction level.

Depending on the size of the screen of the electronic display device, the plurality of processed optotypes is displayed simultaneously or, alternatively, line by line.

For example, the electronic display device displays only one line of processed optotypes at a time. The first line displayed corresponds for instance to processed optotypes with a value of 0 D. When pressing buttons or arrows, the observer may switch the display to another line of processed optotypes having a different value of refraction correction than the first line, corresponding either to positive or negative refraction correction. The device may switch to increasingly higher values of refraction correction P, by a constant step of 1 D, 0.5 D or 0.25 D. The observer then evaluates the line he/she sees more clearly. Alternatively, methods based on well-known limits or staircase methods, or Bayesian estimation are employed for ensuring a very precise and stable estimation of the needed correction.

A person normally not accommodating and not corrected (relax and stable accommodation) sees clear only one line corresponding to his/her level of correction needed.

In a variant, the electronic display comprises a light field display and comprises further at least a multilayer filter or diffractive pattern placed on said electronic display so as to apply a complementary image processing for displaying said processed optotype. For example, an auto-stereoscopic display including an array of cylindrical micro lenses, also called lenticular array, on its screen surface, allows each eye to see a different image and enables three-dimensional vision.

FIG. 3 represents the same optometry measuring scale as generated in FIG. 2H, as a function of different levels of spherical correction (column 3G) but as seen by three different observers having respectively different myopic spherical defects (columns 3H, 3I) or hyperopic spherical defect (column 3J) and not accommodating.

A myopic person looking at far (Dist larger than 4-5 meters) and needing a correction of −3 D sees clearly in column 3H only the line corresponding to −3 D.

In the same manner, a myopic person looking at far (Dist larger than 4-5 meters) and needing a correction of −1 D sees clearly in column 3I only the line corresponding to −1 D.

Similarly, a hyperopic person looking at far (Dist larger than 4-5 meters) and needing a correction of +1 D sees clearly in column 3J only the line corresponding to +1 D.

In the case where the observer is not accommodating, the level of correction needed corresponds to the only lines seen clearly by the observer.

However, when an image is slightly out of focus, a young person normally accommodates. The refractive power of lens of the eye changes within the accommodation amplitude of the eye so as to form a clear image on the retina of the observer.

For example, FIG. 4 shows the same exemplary optometry measuring scale as generated in FIG. 2H, as a function of different levels of spherical correction (column 4G) but as seen by different persons having different visual defects and/or different accommodation amplitudes. Column 4H shows the optometry measuring scale as seen by a myopic person needing a correction of −3 D, looking at far (Dist larger than 4-5 meters) and not accommodating. The only line seen clearly in column 4H corresponds to the needed correction of −3 D for this observer.

Column 4I shows the optometry measuring scale as seen by a myopic person needing a correction of −1 D, looking at far (Dist larger than 4-5 meters) and accommodating within accommodation amplitude up to 2 D. Several lines are seen clearly in column 4I corresponding to levels of correction from −1 D to −3 D. The needed correction for this myopic person corresponds to the first line seen clearly by this person when reading lines down starting from the top line: −1 D.

Column 4J shows the optometry measuring scale as seen by a hyperopic person needing a correction of +1 D, looking at far (Dist larger than 4-5 meters) and accommodating within accommodation amplitude up to 4 D. Several lines are seen clearly in column 4J corresponding to levels of correction from +1 D to −3 D. The needed correction hyperopic person corresponds to the first line seen clearly by this person_when reading lines down starting from the top line: +1 D . . .

Alternatively, for a hyperope person (especially having high value hyperopia, especially above +2 D), it is possible to avoid compensating his/her ametropia by accommodating. This can be done by inserting a positive lens corresponding to a presupposed maximum hyperopia (for example a positive lens of +4 D or +8 D), so that the person sees blurred the non compensated images, and then by adding the compensation corresponding to the line best perceived with the power of the added lens. Alternatively, this can be done using an add-on lens directly on the screen so that the screen is directly seen at infinity.

Figure 5:
FIG. 5 represents the same exemplary optometry measuring scale as seen by a same hyperopic person accommodating respectively without compensation lens (5H) and with different compensation lenses (columns 5I, 5J)

For example, FIG. 5 shows the same exemplary optometry measuring scale as generated in FIG. 2H, as a function of different levels of spherical correction (column 5G) but as seen by a same hyperopic person without positive lens (5H) and respectively with a positive lens of different refractive power (5I, 5J).

Column 5H shows the optometry measuring scale as seen by a hyperopic person needing a correction of +3 D, looking at far (Dist larger than 4-5 meters) and accommodating within an accommodation range up to +6 D. All the lines corresponding to refractive correction from −3 D to +3 D are seen clearly in column 5H, thus not allowing to determine the correction needed.

Column 5I shows the same optometry measuring scale as seen by the same hyperopic person needing a correction of +3 D, looking at far (Dist larger than 4-5 meters) and equipped with a compensation lens of +4 D refractive power. All the lines corresponding to refractive correction from −3 D to −1 D are seen clearly in column 5I. Taking into account the value of the compensation lens, the first line seen clearly (−1 D), when this person reads from the top line to the bottom line, is the line corresponding to −1 D: this enables to determine the actual correction needed of +3 D (+4 D−1 D=+3 D).

Column 5J shows the same optometry measuring scale as seen by the same hyperopic person needing a correction of +3 D, looking at far (Dist larger than 4-5 meters) and equipped with a compensation lens of +6 D refractive power. The first and only line seen clearly in column 5J corresponds to a refractive correction of −3 D. Thus, the compensation lens of high refractive power prevents the hyperopic person from accommodating, and enables to determine the correction needed of +3 D (=+6 D−3 D).

The examples shown in FIGS. 2-5 enable evaluating spherical correction for emmetrope, myopic or hyperopic persons very quickly.

Another optometry measuring scale can be used for evaluating cylindrical compensation needed and/or for evaluating cylindrical axis orientation.

FIG. 6 shows the generation process of another exemplary optometry measuring scale (table 6H) as a function of the level of spherical correction (column 6G) combined with the level of cylindrical correction (column 6K).

FIG. 6, column 6E, shows the initial target, or source optotypes, for example a single Snellen's E.

Column 6F represents a computation process used for generating processed optotypes, as a function of different levels of spherical correction displayed in column 6G and, respectively as a function of different level of cylindrical correction displayed in line 6K. Typically for a cylindrical error Cyl of axis axe, the phase error is expressed as a function of the position in the pupil $p(r,teta)=-Cyl*r^2*\sin^2(teta-axe)/2$ where (r,teta) are polar coordinates of the position in the pupil. Alternatively, this phase error can be combined with a spherical phase error and/or with a phase error of any other type. For example, for a cylindrical error Cyl of axis axe combined with a spherical error P, the phase error will be expressed as $p(r,teta)=r^2/2*(P+Cyl*\sin^2(teta-axe))$.

Table 6H represents processed optotypes as seen by an observer not needing visual correction and not accommodating. Each line of table 6H corresponds to a line of optotypes processed with a spherical error corresponding to the level indicated in column 6G, ranging from −3 D to +3 D, in steps of 1 D.

Each column of table 6H corresponds to a column of processed optotypes, processed with a cylindrical error corresponding to a given orientation and to the level of cylindrical correction indicated in line 6K, from 0 D to 3 D, in steps of 1 D, combined with the relevant spherical correction.

Each optotype in table 6H thus corresponds to a single combination of a spherical correction value and to a cylindrical correction value of axis 0°.

For an observer having an emmetrope vision and not accommodating, only the optotype corresponding to 0 D spherical correction and 0 D cylindrical correction is seen clearly, all the other processed optotypes in table 6H appearing blurred.

For other observers, the determination of the line (sphere) and column (cylinder) corresponding to the best perceived image of processed optotype enables to evaluate both sphere and cylinder correction needed, and the corresponding sphere and cylinder correction values.

Different preprinted tables, corresponding to different cylinder axis with predefined orientation axis of 0, 45, 90, 135 degrees for example can be used to evaluate grossly the orientation of the cylinder axis.

Alternatively, a single table, with a defined cylindrical axis orientation of 0 degrees, can be rotated in its plane by decreasing steps of rotation angles starting from 90 degrees to 1°.

In another alternative embodiment, the cylinder axis is evaluated first using a Parent dial. A table corresponding to the determined axis is then used for evaluating cylindrical correction value.

In another alternative embodiment, a table as shown on FIG. 6H is displayed on the screen of a mobile system such as a smartphone or tablet. A software application advantageously uses the internal gyroscope of this mobile system to compensate the screen orientation for a proper orientation of the displayed cylinder axis correction.

The step of correction between each line in the optometry scale of FIG. 2 (and/or each column of the optometry table of FIG. 6) can be varied. A first optometry scale may use a step of 1 D between lines. After, a first evaluation of the correction needed, another optometry scale can be presented using a step of 0.5 D/line or 0.25 D/line and, eventually 0.12 D/line, according to the sensitivity of the subject's responses.

The range of the scale of spherical refraction is generally comprised between −3 D and +3 D. However, these values are given only as examples and do not limit the scope of the present disclosure. The range of spherical correction can be enlarged as necessary according to the desired size of the optometry scale and to the step between lines. In general, a scale of spherical correction level ranging from −10 D to +6 D with a step of 0.5 D is advisable for evaluating ametropia of most of the population. However, any other combination of range and step is feasible. For evaluating astigmatism, the scale ranging from −4 D to 0 D by step of 0.5 D is advisable.

Alternatively, the level of astigmatism may be displayed in lines, and the level of spherical correction (ametropia) may be displayed in columns.

Process

A process for evaluating visual refraction correction in far distance vision conditions can be applied to a large group of people. An optometry measuring scale is displayed so that all the people placed in a room can look together simultaneously at the scale at a distance of at least 3-4 meters. In this case, it is preferable that the horizontal field of view of the optometry measuring scale is more than +−45 degrees.

Each person attending the visual test notes the best perceived line (and/or column) in the optometry measuring scale.

For example, an optometry measuring scale based on a printed scale displaying processed optotypes (or modified images) corresponding to different corrections can be used in a dispensary of developing countries, in which access to professional eye care is limited. In this case, the optometry measuring scale may consist in a simple paper poster easy to carry and install in a room allowing a large group of people to see the targets. This solution is very cheap, portable and facilitates mass screening without any intervention of a qualified person. Each person undergoing the test can write down or check mark on a form the highest number of the line he/she perceives with reduced or no blur. This can be done for different tests including different levels of spherical correction, and/or cylinder correction and axis correction. At the end of the test, it is so possible to propose a corrective lens including the correct refraction level (RX), based on the answer provided by the person himself/herself on the form.

This solution can also be used for near vision screening. Using a near vision scale, the distance Dist (typically lower than 50 cm) between the person and the support 10 can be fixed. Alternatively, the distance Dist is varied and the person notes, for each distance Dist, the best perceived line: the result of these tests enables evaluating the accommodation response as a function of the distance Dist.

The needed addition for comfortable near vision is easily derived from the combination of far vision and near vision optometry measurements. As a practical rule, the addition is chosen so that the accommodation will be limited to less than 66% of the tested maximum accommodation available for the subject, or even to less than 50% of the maximum accommodation for elder people.

For example, if the near distance is fixed, a prepared chart provides the visual refraction correction value based on the following formula:

$$P = 1/\text{Dist} - 1/D_{target}$$

for P=0 D, P=0.5 D, P=1 D, P=1.5 D, P=2 D, P=2.5 D
$D_{target}$ is determined according to D and to Dist.
For example, if Dist=25 cm, Dtarget=25 cm for P=0 D, and Dtarget=66.6 cm for P=1 D.

Then, the person undergoing the test (who is for example supposed to be emmetrope and presbyope) is asked to select the first test he/she perceives clearly and not blurred.

For example, if the person states that the optotype corresponding to 0 D is not blurred, it means that this person has no lack of accommodation at this distance. In contrast, if the person states that the optotype corresponding to 1 D is the first to be perceived not blurred, it means that this person has a lack of 1 D for accommodation (accommodation capacity is 1.5 D at 40 cm).

This test enables evaluating the lack of accommodation or accommodation capacity of the observer. Then, a progressive/multifocal lens having at least an addition corresponding to the test result may be proposed to the tested person.

In the present disclosure, accommodation capacity or accommodation amplitude is the possible accommodation response. For example, a subject being at a distance of 40 cm, the required accommodation to see sharply is 2.5 D. If a residual defect of 1 D is measured, thus the accommodation amplitude of this subject is only 1.5 D.

FIG. 7 shows the same optotypes as in FIG. 2, in column 7E and the processed optotypes in column 7H. However, the scale displayed in column 7G displays two diopter levels for each line: the left value corresponds to the level of correction needed and, the right value in parenthesis corresponds to the accommodation capacity, for a near vision distance of 40 cm. FIG. 7 shows an example of test for determining lack of accommodation and/or addition as seen at a distance of 40 cm by an emmetrope person having only 1.5 D accommodation capacity. The first line seen clearly by this person is the line of optotypes corresponding to 2.5 D at far distance and to OD at near distance of 40 cm: thus, this person does not need correction for near vision. All the lines from OD (accommodation capacity scale) to 1.5 D (accommodation capacity scale) are seen clearly by this person: thus, this person has an accommodation capacity of 1.5 D in near vision conditions.

This method can also be implemented for a screening through the internet web without additional hardware for the display. The only prerequisite is that the accommodation of the tested person is stable and known. For example, the screen is placed at a known distance of at least 2m. Alternatively, the electronic device may comprise a detection system, for example based on a webcam, for determining the distance between the person and the screen. In this case, the optometry scale is display sequentially line by line, or even optotype by optotype, as a function of a varying correction level. The step of varying correction level between sequential displayed modified optotypes can be fixed to 1 D, 0.5 D, 0.25 D or even 0.12 D. Alternatively, a dynamically refined psychophysical protocol enables to adjust the correction level between successive correction levels of the displayed modified optotypes. For instance the well-known dichotomy, limits or staircase methods or a Bayesian estimation may be used for converging faster to the final correction level needed. All these methods allow determining the level of a needed correction with a step lower than the subjective detection limit of the subject and/or with a better reproducibility.

Compared to a static optometry measuring scale, the use of an electronic device implementing the present disclosure is generally preferred for the following reasons:

It enables to propose a very large set of tests using the same device to determine refraction correction level (RX) for different parameters (sphere S, and/or cylinder C and axis A). It also enables to propose different optotypes according to the culture (Chinese/Indian/latin/greek/Cyrillic characters) or to the age of the person (Adult/Child) or the education of the persons.

The modified target (to display the virtual distance) may be different depending on the distance Dist between the wearer and the display, and this distance may not be fixed. Thus, the target can be dynamically modified to take into account the actual distance Dist, especially for near vision test. The actual distance Dist can be measured using an embedded detection system or a stereo camera mounted on the electronic device.

It is possible to use input means to store the answer of the person. Algorithms in the electronic device may be implemented to modify dynamically the tests according to the previous answer from the person, in order to refine the prescription.

Thus, the invention provides a method to determine refraction using a specific display for presenting an optometry measuring scale. The optometry measuring scale displays modified target images that modify blurriness perceived by the eye(s) of a person. Displaying (simultaneously or sequentially) a set of different modified targets having different blurriness levels, and asking the person to identify the less blurred perceived target, enables to determine the level of visual correction needed (RX) according to the answer.

The invention claimed is:

1. An optometry measuring scale for determining a visual refraction value of an individual, said optometry measuring scale comprising:
    a plurality of processed optotypes associated with a plurality of visual refraction corrections, each processed optotype resulting from applying to a source optotype a determined image processing associated with a defined visual refraction correction, the determined image processing comprising applying to the source optotype that has a high constrast and a high clearness a deconvolution algorithm by a complex amplitude function representative of spherical phase error and/or cylindrical phase error and as a function of a predefined vision distance or a predefined display distance; and
    an identification system configured to determine each defined visual refraction correction associated with each processed optotype.

2. The optometry measuring scale according to claim 1, wherein the optometry measuring sale is configured to simultaneously display a plurality of processed optotypes.

3. The optometry measuring scale according to claim 1, further comprising first and second processed optotypes associated with a same defined visual refraction correction and, respectively, with a first vision distance and a second vision distance, wherein said first and second processed optotypes result from applying to a source optotype a determined image processing associated with said same defined visual refraction correction, and respectively, with said first vision distance and with said second vision distance.

4. The optometry measuring scale according to claim 1, wherein said defined visual refraction correction includes a spherical error correction and/or a cylindrical error correction.

5. The optometry measuring scale according to claim 1, further comprising an electronic display device, wherein said source optotype comprises a digital image to be displayed on said electronic display device.

6. The optometry measuring scale according to claim 5, wherein said electronic display comprises a light field display comprising at least a multilayer filter or diffractive pattern placed on said electronic display so as to apply a complementary image processing for displaying said processed optotype.

7. The optometry measuring scale according to claim 1, further comprising at least one pre-printed chart to display a plurality of processed optotypes.

8. The optometry measuring scale according to claim 1, wherein said source optotype is selected among Landolt rings, Snellen's E, alphanumerical characters or images used to measure visual acuity.

9. The optometry measuring scale according to claim 1, wherein the processed optotypes are arranged in lines, wherein each line corresponds to a same determined image processing associated with a same defined visual refraction correction applied to one or different source optotypes.

10. The optometry measuring scale according to claim 1, wherein the pre-processed optotypes are arranged in lines and columns, and
    wherein each column corresponds to a pre-defined visual refraction parameter chosen among sphere, cylinder, axis and each line corresponds to another pre-defined visual refraction parameter chosen among a sphere, a cylinder, and an axis, the pre-defined visual refraction parameter of the columns being different from the pre-defined visual refraction parameter of the lines.

11. The optometry measuring scale according to claim 9, wherein the defined visual refraction correction changes gradually from line to line and/or from column to column, by step of 1 diopter, ½ diopter, ¼ diopter or ⅛ diopter.

12. A method for determining a visual refraction correction for a user, the method comprising:
    providing the optometry measuring scale of claim 1; and
    applying the optometry measuring scale to determine the visual refraction correction.

13. An optometry measuring method comprising:
    displaying a plurality of processed optotypes associated with a plurality of visual refraction corrections, wherein each processed optotype results from applying to a source optotype a determined image processing associated with a defined visual refraction correction, the determind image processing comprising applying to the course optotype that has a high constract and a high clearness a deconvolution algorithm by a complex amplitude function representative of spherical phase error and/or cylindrical phase error and as a function of a predefined vision distance or a predefined display distance;
    displaying an identification system to determine each defined visual refraction correction associated with each processed optotype;
    determining the sharpest processed optotype as seen by a user;
    determining a defined visual refraction correction associated with the sharpest processed optotype seen by the user; and
    evaluating, from the defined visual refraction correction determined at the previous step, the visual refraction correction needed for the user.

14. The optometry measuring method according to claim 13, wherein the processed optotypes are arranged in lines, and
    wherein each line corresponds to a same determined image processing associated with a same defined visual refraction correction applied to one or different source optotypes.

15. The optometry measuring method according to claim 14, wherein the defined visual refraction correction changes gradually from line to line, within a range comprised between −10 diopters and +6 diopters, by steps of 1 diopter, ½ diopter, ¼ diopter or ⅛ diopter.

16. The optometry measuring scale according to claim 3, further comprising at least one pre-printed chart to display a plural of processed optotypes.

17. The optometry measuring scale according to claim 4, further comprising an electronic display device, wherein said source optotype comprises a digital image to be displayed on said electronic display device.

18. The optometry measuring scale according to claim 4, further comprising at least one pre-printed chart to display a plurality of processed optotypes.

19. Optometry measuring scale according to claim 10, wherein the defined visual refraction correction changes gradually from line to line and/or from column to column, by step of 1 diopter, ½ diopter, ¼ diopter or ⅛ diopter.

* * * * *